United States Patent [19]

Bargar et al.

[11] Patent Number: 4,703,058

[45] Date of Patent: Oct. 27, 1987

[54] β-METHYLENE FURANETHANAMINES AND USE AS ANTI-HYPERTENSIVE AGENTS

[75] Inventors: Thomas M. Bargar, Zionsville; Robert Broersma, Jr., Noblesville; James R. McCarthy, Zionsville, all of Ind.

[73] Assignee: Merrell Dow Pharmaceuticals Inc., Cincinnati, Ohio

[21] Appl. No.: 871,656

[22] Filed: Jun. 6, 1986

Related U.S. Application Data

[63] Continuation of Ser. No. 687,627, Dec. 31, 1984, abandoned.

[51] Int. Cl.[4] .................... A61K 31/34; C07D 307/52
[52] U.S. Cl. .................... 514/471; 549/491; 549/492
[58] Field of Search .................. 549/491, 492; 514/471

[56] References Cited

U.S. PATENT DOCUMENTS 4,454,158  6/1984  Bey .................................. 549/491 X

OTHER PUBLICATIONS

J. B. Van der Schoot et al., *Arzneimittel-Forschung*, 12(9), 902 (1962).
Kaufman, S.; Friedman, S. *Pharm. Rev.*, 1965, 17, 71.
Pieschi, L.; Oehlke, J.; Schoretter, E.; Oehme, P., *Pharmazie*, 1983, 38, 355.
Hidaka, H. *Nature (London)* 1971, 231, 54.
Mangold, J. B.; Klinman, J. P., *J. Biol. Chem.* 1984, 259, 7772.
Colombo, G.; Rajaskekar, B.; Giedioc, D. P.; Villafrance, J. J., *J. Biol. Chem.* 1984, 259, 1593.
(a) Rajashekar, B.; Fitzpatrick, P. F.; Colombo, F.; Villafranca, J. J., *J. Biol. Chem.* 1984, 259, 6925, (b) Fitzpatrick, P. F.; Flory, D. R.; Villafranca, J. J., *Biochemistry* 1985, 24, 2108.
Colombo, G.; Villafranca, J. J., *J. Biol. Chem.* 1984, 259, 15017.
May, S. W.; Mueller, P. W.; Padgette, S. R.; Herman, H. H.; Philips, R. S., *Biochem. Biophys. Res. Commun.* 1983, 110, 161.
Creveling, C. R.; van der Schoot, J. B.; Udenfriend, S., *Biochem. Biophys. Res. Commun.* 1962, 8, 215.
Hori, T.; Sharpless, K. B., *J. Org. Chem.* 1979, 44, 4204.
Overman, L. E., *J. Am. Chem. Soc.* 1976, 98, 2901.
Klemm, L. M.; McGuire, T. M.; Gopinath, K. W., *J. Org. Chem.* 1976, 41, 2571.
Aunis, D.; Murias-Portugal, M. T.; Mander, P. J., *Neurochemistry* 1975, 24, 425.
Kitz, R.; Wilson, T. B., *J. Biol. Chem.* 1962, 237, 3245.

*Primary Examiner*—Richard L. Raymond
*Attorney, Agent, or Firm*—Raymond A. McDonald; John J. Kolano

[57]  ABSTRACT

This invention relates to novel β-methylenefuranethanamines which are mechanism-based inhibitors of dopamine beta-hydroxylase useful as antihypertensive agents.

4 Claims, No Drawings

β-METHYLENE FURANETHANAMINES AND USE AS ANTI-HYPERTENSIVE AGENTS

CROSS-REFERENCE TO RELATED APPLICATION

This is a continuation of application Ser. No. 687,627, filed Dec. 31, 1984, now abandoned.

This invention relates to novel allylic amines, the processes and intermediates useful for their preparation, and to the pharmaceutical compositions and the method of treating hypertension with such compositions.

More specifically, this invention relates to allylic amines of the formula

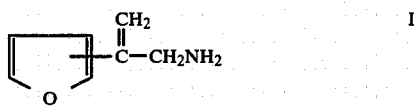

and the non-toxic pharmaceutically acceptable acid addition salts thereof. Still more specifically, the compounds of this invention relate to β-methylene-2-furanethanamine and β-methylene-3-furanethanamine and the non-toxic pharmaceutically acceptable acid addition salts thereof.

Representative salts are those salts formed with non-toxic organic or inorganic acids, such as, for example those formed from the following acids: hydrochloric, hydrobromic, sulfonic, sulfuric, phosphoric, nitric, maleic, fumaric, benzoic, ascorbic, succinic, methanesulfonic, acetic, propionic, tartaric, citric, lactic, malic, mandelic, cinnamic, palmitic, itaconic, and benzenesulfonic.

The allylic amines (I) of this invention can readily be prepared by a series of reactions illustrated by the following reaction scheme:

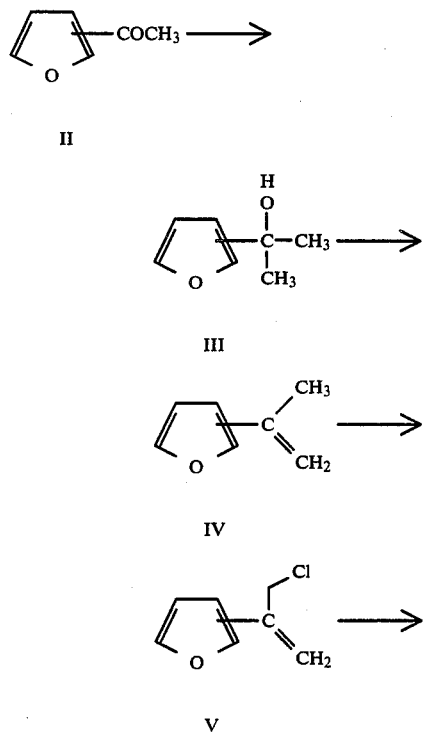

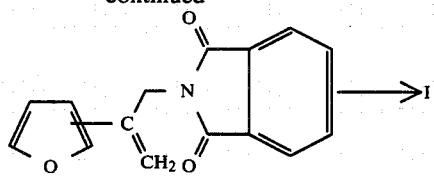

In essence, the foregoing reaction scheme depicts the conversion of 2- or 3-acetyl derivatives of furan to the corresponding 2- or 3-isopropylidene derivatives by reactions with methylmagnesium bromide with subsequent dehydration according to standard Grignard reaction conditions. The isopropylidene derivatives (IV) are subjected to allylic chlorination according to standard conditions and the crude products (IV) are converted (via phthalimide derivatives (V)) by the well-known Gabriel synthesis to obtain the desired allylic amines of formula I. The free bases can be converted to the acid addition salts, or the acid addition salts can be converted to the free bases, by conventional chemical methodology.

The foregoing reaction scheme is further illustrated by the following specific exemplifications.

EXAMPLE I

β-Methylene-2-Furanethanamine Hydrochloride

Step A: 2-(1-Methyl)ethyenylfuran

A solution of 55.06 g (0.5 mole) of 2-acetylfuran in 100 ml of anhydrous ether was added dropwise under $N_2$ during 1.5 hour to 211 ml of 2.85M methylmagnesium bromide/ether (0.6 mole) while the reaction mixture was stirred in an ice bath. The temperature was kept below 30° C. by controlling the rate of addition. A grey precipitate formed. The mixture was allowed to warm to 25° C. for 1 hour, then was cooled again in an ice bath while 100 ml of saturated $NaHCO_3$ solution was added carefully. The resulting mass was dissolved in about 1 liter of water and the aqueous phase was extracted twice with ether. The combined ether solutions were extracted with saturated NaCl solution, dried over $K_2CO_3$, filtered, and concentrated at atmospheric pressure to a yellow oil. To this crude alcohol was added 5.0 g of $KHSO_4$ and about 0.1 g of 4-tert-butyl catechol (inhibitor) and the mixture was distilled at 1 atm. A mixture of the desired product and water distilled over at about 90° C. The water was separated and the product was dried over $K_2CO_3$, then filtered to afford 8.5 g of colorless oil. Similarly prepared is 3-(1-methyl)ethenylfuran.

Step B: N-2-(2-Furanyl)propenylphthalimide

To a solution of 8.35 g (0.077 mole) of the olefin of Step A in 310 ml of DMF was added 12.37 g (0.093 mole) of N-chlorosuccinimide and 1.46 g (0.0047 mole) of diphenyl diselenide. After 3 hours at room temperature the mixture was partitioned between 500 ml of hexane and 1000 ml of 5% $Na_2S_2O_3$. The hexane was distilled off at atmospheric pressure and the residue was dissolved in 200 ml of DMF, 9.49 g (0.051 mole) of potassium phthalimide was added and the mixture was warmed to 90° C. under $N_2$. After 45 min. the cooled reaction mixture was poured into water and the precipitated product was filtered off and recrystallized from ethylacetate/2-propanol, affording 3.57 g colorless crystals, mp. 136°–137° C.

Anal. Calc'd for $C_{15}H_{11}NO_2S$: C, 66.90; H, 4.12; N, 5.20. Found: C, 66.82; H, 4.30; N, 4.97.

Similarly prepared is N-2-(3-furnayl)propenylphthalimide.

Step C: β-Methylene-2-furanethanamine HCL

To a magnetically stirred suspension of 3.50 g (13.83 mmol) of the phthalimide prepared in Step B was added 1.34 ml (27.64 mmol) of hydrazine hydrate and the mixture was refluxed under $N_2$ for 1 hour, during which time a thick precipitate formed. The cooled mixture was distilled with 1M KOH to dissolve the precipitate, then was extracted with ether. The ether layer was washed with 1M KOH, then was extracted with 1M HCl. The acid layer was made basic with 5N NaOH, then was saturated with NaCl and extracted with ether. The ether phase was dried over $K_2CO_3$ and concentrated to a yellow oil. Distillation afforded 1.23 g of colorless liquid, bp 40° C. at 0.5 torr. The amine was taken up in ether, cooled in an ice bath, and a saturated solution of anhydrous HCl in ether was added dropwise unit no more precipitate formed. The volatiles were removed under vaccum and the residue was recrystallized from ethanol/ethyl acetate to afford 1.2 g colorless crystals, mp 150°–151° C.

Anal. Calc'd for $C_7H_9NO \cdot HCl$: C, 52,68; H, 6.31; N, 8.78. Found: C, 52.48; H, 6.43; N, 8.61.

Similarly prepared is β-methylene-3-furanethanamine. HCl.

The allylic amines of this invention (I) are dopamine β-hydroxylase (DBH) inhibitors in a mechanism-based fashion; inactivation being time, and concentration dependent. Thus the compounds of formula I are expected to be valuable therapeutic agents useful in the treatment of hypertension.

The dopamine β-hydroxylase inhibitory properties of the compounds of this invention can readily be determined by standard and well known procedures such as those procedures set forth in U.S. Pat. No. 4,415,191. For example, determination of whether the DBH inhibition allows time-dependent kinetics is exemplified by the procedure wherein enzymatic oxygenation by DBH is determined in aqueous solution in the presence of molecular oxygen, an electron donor such as ascorbate, and the necessary cofactors for the enzyme at a pH of 5 and a temperature of 20°–40° C., preferrably 37° C. The test compound is added at the desired concentration, and the system is incubated. At different time intervals, aliquots are taken and DBH activity is measured using tyramine as the substrate and the reaction followed by measuring the oxygen uptake using a polarographic electrode and an oxygen monitor by the method of S. May et al., J. Biol. Chem. 256, 2258 (1981). The inhibition constants for the inactivation of DBH by each compound are then determined by conventional procedures such as the method of Kitz and Wilson, J. Biol. Chem. 237, 3245 (1962). When the compound shown in Table I was tested according to the above described procedure, the DBH inhibitory activity increased as a function of the time of incubation. The initial rate of decrease of activity increased with increasing concentration of inhibitor. The results in Table I indicate that β-methylene-2-furanethanamine is potent as illustrated by the rapid rate of inactivation ($k_{inact}$) and low inhibition contant ($K_I$).

TABLE I

| DBH INHIBITORY ACTIVITY - IN VITRO | | |
|---|---|---|
| Compound | $K_I$ (mM) | $K_{inact.}$ (min$^{-1}$) |
| β-Methylene-2-Furanethanamine | 8 | 0.004 |

TABLE II

| ANTIHYPERTENSIVE ACTIVITY - IN VIVO | | |
|---|---|---|
| Compound | Dose mg/kg | Maximum % Change Mean Blood Pressure |
| β-Methylene-2-Furanethanamine | 10 (ip) | 18 |
| | 30 (ip) | 32 |

The ability of the compounds of this invention to lower blood pressure can be determined in vivo using hypertensive rats according to standard and well known procedures. The test compound is administered intraperitoneally (ip) or orally (po) to rats and the blood pressure monitored continuously. Since DBH is a major enzyme in the synthetic pathway of the catecholamines, it would be expected that the presence of an inhibitor would act to decrease the amount of catecholamines produced, and thereby have an antihypertensive effect. The results of the testing for this antihypertensive effect are shown in Table II.

Thus, based upon these and other standard laboratory techniques known to evaluate dopamine β-hydroxylase inhibitors, by standard toxicity tests and by standard pharmacological assay for the determination of antihypertensive activity in mammals, and by comparison of these results with the results with known antihypertensive agents, the effective antihypertensive dosage of the compounds of this invention can readily be determined. In general, effective antihypertensive results can be achieved at a dose of about 5 to about 100 mg per kilogram of body weight per day. Of course the specific initial and continuing dosage regimen for each patient will vary according to the nature and severity of the hypertension as determined by the attending diagnostician.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms as, for example, tablets, capsules and suppositories, or in liquid forms, as for example, elixirs, emulsions, sprays and injectables. In the formulation of pharmaceutical preparations there can be employed such substances which do not react with active substance as, for example, water, gelatin, lactose, starches, magnesium sterate, talc, vegtable oils benzyl alcohols, gums, polyalkylene glycols, petroleum jelly and the like. The active ingredient of such pharmaceutical preparations is preferably present in the preparation in such proportions by weight that the proportion by weight of the active ingredient to be administered lies between 0.1% and 50%.

We claim:

1. A compound of the formula

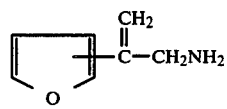
and the non-toxic pharmaceutically acceptable acid addition salts thereof.
2. A compound of claim 1, said compound being β-methylene-2-furanethanamine.
3. A compound of claim 1, said compound being β-methylene-3-furanethanamine.
4. A method of treating hypertension in mammals which comprises administering to said mammal an effective amount of an allylic amine of claim 1.
* * * * *

UNITED STATES PATENT AND TRADEMARK OFFICE
CERTIFICATE OF CORRECTION

PATENT NO. : 4,703,058
DATED : October 27, 1987
INVENTOR(S) : T.M. Bargar; J.R. McCarthy; R. Broersma, Jr.

It is certified that error appears in the above-identified patent and that said Letters Patent is hereby corrected as shown below:

At Column 2, line 19, the patent reads "products (IV)" and should read --(V)--.

At Column 2, Line 20, the patent reads "(V))" and should read --(VI)--.

At Column 2, Line 31, the patent reads "ethyenylfuran" and should read --ethenylfuran--.

Signed and Sealed this

Twenty-ninth Day of August, 1989

Attest:

DONALD J. QUIGG

Attesting Officer

Commissioner of Patents and Trademarks